United States Patent [19]

Egan et al.

[11] 4,247,425
[45] Jan. 27, 1981

[54] LIGHT DUTY NON-IRRITATING DETERGENT COMPOSITIONS

[75] Inventors: Richard R. Egan, Worthington; Phillip L. Cotrell, Urbana, both of Ohio

[73] Assignee: Sherex Chemical Company, Inc., Dublin, Ohio

[21] Appl. No.: 36,706

[22] Filed: May 7, 1979

Related U.S. Application Data

[63] Continuation of Ser. No. 942,075, Sep. 13, 1978, abandoned, which is a continuation-in-part of Ser. No. 848,978, Nov. 7, 1977, abandoned.

[51] Int. Cl.³ .......................... C11D 1/12; C11D 1/83
[52] U.S. Cl. .............................. 252/548; 252/174.22; 252/550; 252/551; 252/558; 252/559; 252/DIG. 14
[58] Field of Search ...................... 252/174.21, 174.22, 252/550, 551, 547, 548, 558, 559, DIG. 14, 545

[56] References Cited

U.S. PATENT DOCUMENTS

| | | | |
|---|---|---|---|
| 3,532,636 | 10/1970 | Pacini | 252/558 X |
| 3,538,009 | 11/1970 | Kelly | 252/558 X |
| 3,813,350 | 5/1974 | Kelly | 252/547 |
| 3,944,663 | 3/1976 | Weiss et al. | 424/78 |
| 3,947,384 | 3/1976 | Kelly et al. | 252/542 |

FOREIGN PATENT DOCUMENTS 46-14340 4/1971 Japan .
1540386 2/1979 United Kingdom ................ 252/174.22

Primary Examiner—P. E. Willis, Jr.
Attorney, Agent, or Firm—Burton A. Amernick; Edward B. Dunning

[57] ABSTRACT

A liquid detergent system wherein the active content is a combination of an anionic surfactant and a nonionic surfactant in the form of alkoxylated partial glycerol esters of a detergent grade fatty acid and optionally containing a foam stabilizing agent. The indicated nonionics are characterized in having a polyoxyalkylene chain composed of randomly distributed oxyethylene and oxypropylene residues. These systems are particularly useful for formulating shampoos and light duty liquid household cleaning compositions having low eye and skin irritation properties.

8 Claims, 1 Drawing Figure

| BLENDS | 82(3EO/PO) GLYCERYL TALLOWATE | 35(3EO/PO) GLYCERYL COCOATE |
|---|---|---|
| BLEND 1 | 67% | 33% |
| BLEND 2 | 50% | 50% |
| BLEND 3 | 33% | 67% |

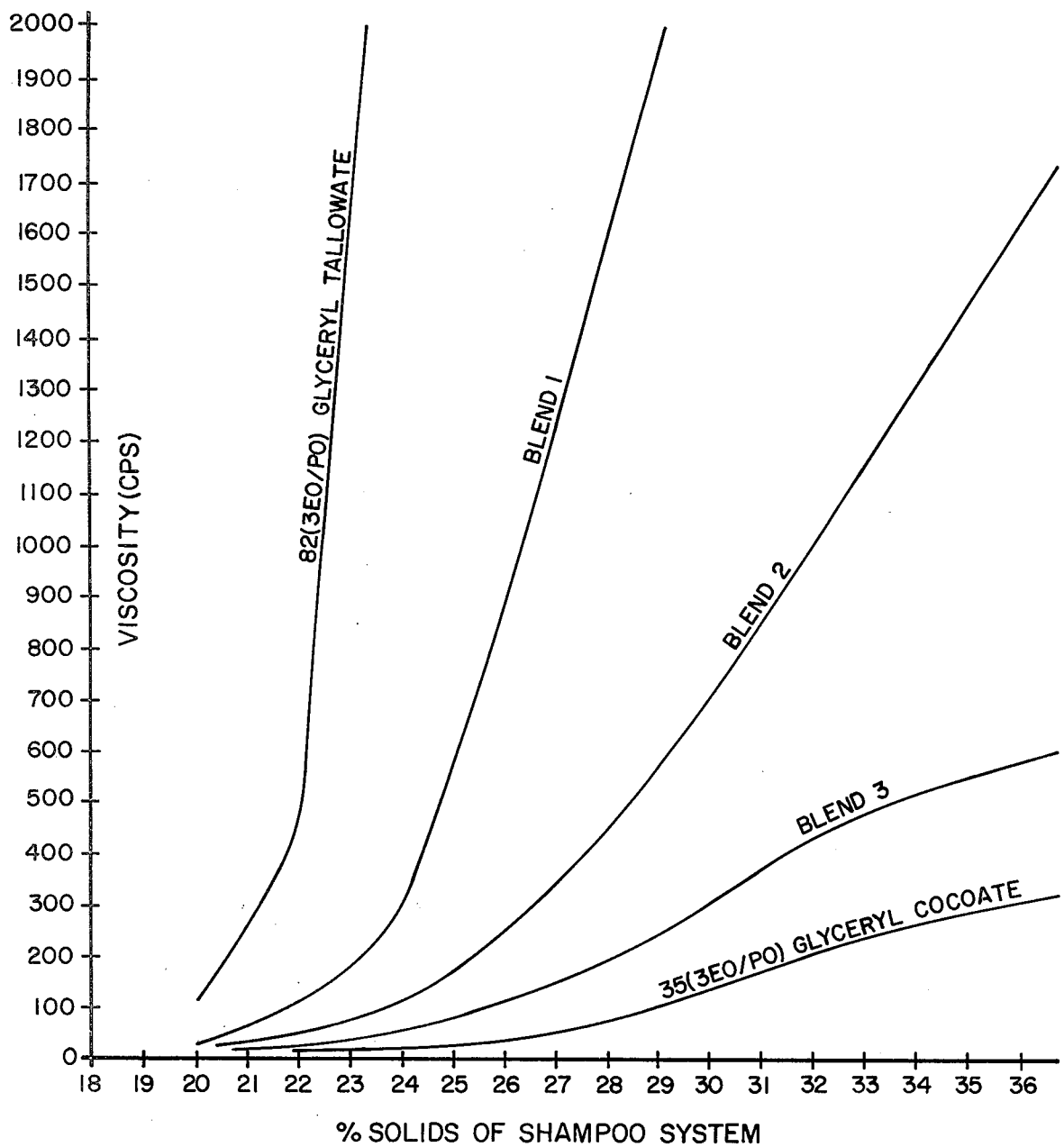

# 4,247,425

LIGHT DUTY NON-IRRITATING DETERGENT COMPOSITIONS

This is a continuation of application Ser. No. 942,075, filed Sept. 13, 1978, now abandoned, which in turn is a continuation-in-part application of Ser. No. 848,978, filed Nov. 7, 1977 (now abandoned).

BACKGROUND OF THE INVENTION

1. Field of the Invention

This invention relates to liquid detergent compositions.

2. Description of the Prior Art

To date, most shampoos and light duty household detergent products have been based on the combination of an anionic surfactant and a surface active agent serving as a foam promoter or stabilizer. Exemplary of the anionics for these applications include sodium lauryl sulfate, (SLS), sodium lauryl ether sulfate (SLES) and linear alkyl benzene sulfonate (LAS). Generally, the foam promoter is a tertiary amine oxide or an alkanolamide, either of the so-called superamide or of the Kritchevsky type.

All of the aforementioned surface active agents and particularly the anionics are severe eye irritants and are capable of causing mild to moderate skin irritation to some sensitized persons. Lately, there has been a trend toward substantially ameliorating the irritant effects of such compositions by using the anionic in conjunction with an amphoteric type surfactant and combining these compounds with a nonionic surfactant in the form of an ethoxylate of a partial polyol ester of a higher fatty acid.

The state of the art products of this type, such as the so-called baby shampoo formulations, range in the category of "mildly irritating" in accordance with the Draize eye irritation test. While it would be desirable to provide even blander systems in this respect than are now available, the overriding desideratum, however, is that of obtaining like systems which affords the formulator acceptable latitude in regulating viscosity characteristics of the final products. Most detergent compositions of the type herein concerned are marketed as water solutions containing from about 10 to 30 percent active content. About the only means for regulating viscosity at the indicated range of solid content for the prior art systems necessitates the inclusion of common salt. But this expediency is self-defeating inasmuch as the added salt significantly increases the eye irritation properties of the product.

OBJECT OF THE INVENTION

It is accordingly the object of this invention to provide liquid detergent compositions, particularly shampoos, exhibiting improved eye irritation properties and whose viscosity characteristics can be varied extensively without the inclusion of salt in the formulation for achieving such control.

SUMMARY OF THE INVENTION

In accordance with this invention a low irritation detergent system is provided for formulating household aqueous cleaning compositions which consist essentially of a combination of a nonionic surfactant in the form of an ethylene oxide/propylene oxide adduct of partial glycerol esters of a detergent grade fatty acid and an anionic surface active agent in the form of a salt of a higher alkyl sulfate or sulfonate, a salt of a higher alkyl ether sulfate and a salt of a higher alkyl benzene sulfonate, and which combination optionally includes a foam stabilizing amount of an alkanolamide or a tertiary amine oxide. The relative proportion the nonionic weightwise to the anionic surfactant represents the factor in controlling the irritation level of the system.

An important aspect of the present invention beyond that of providing detergent systems having minimal eye irritation properties resides in the ability to vary extensively the viscosity of dilute aqueous solutions thereof through the appropriate choice of the nonionic surfactant component. By design, the nonionic surfactants useful herein are liquid products at room temperature thus sumplifying handling characteristics thereof in preparing the contemplated detergent systems.

BRIEF DESCRIPTION OF THE DRAWING

The drawing graphically illustrates a manner whereby the viscosity of a typical shampoo formulation at a conventional range of solids content can be varied by appropriately altering the lipophilic characteristics of the non-ionic surfactant component.

DESCRIPTION OF THE PREFERRED EMBODIMENT

The anionic surfactants useful in the practice of this invention are standard items of commerce and hence need not be further elaborated upon herein. Applicable salts thereof are those of an alkali metal hydroxide, preferably sodium hydroxide, ammonium hydroxide, a hydroxy alkyl amine, etc. The contemplated nonionic surfactants although available from commercial sources nevertheless warrant a brief description as to how they can be made. As will be brought out later, there may be a need for having these products tailor-made so as best to meet the particular requirements of the detergent formulator from the standpoint of viscosity control.

The nonionic surfactants are derived from partial glycerol esters of a higher fatty acid. The applicable higher fatty acids are the saturated or unsaturated, preferably the saturated type, of the so-called detergent grade acids having a carbon atom content of from about 10 to 18. Such partial esters consist essentially of a mixture of monoglycerides and diglycerides. The broadly applicable partial esters of this type have a monoglyceride content of from about 15 to 45 wt. %. More preferably, the monoglyceride content $(\alpha+\beta)$ ranges from about 25 to 35 wt. %. As indicated, the balance of the partial ester product will be predominantly the corresponding diglyceride.

These mono- and diglyceride mixtures can be readily prepared by the glycerolysis of a triglyceride in the presence of a basic catalyst, preferably an alkali metal hydroxide. Alternatively, they can be prepared by directly esterifying glycerin with the fatty acids. The molar ratio of triglyceride to glycerin can be adjusted in carrying out the preferred glycerolysis method to result in a reaction product having a monoglyceride content hereinabove specified. In accordance with this procedure, a mole of the triglyceride is transesterified with slightly in excess of one mole of glycerin to yield a product having the preferred monoglyceride content.

The nonionic surfactants useful herein are the alkylene oxide adduct of the partial glycerol esters described above. They are structurally characterized in general as having a polyoxyalkylene chain of randomly distributed oxyethylene and oxypropylene residues in the ratio of 2:1::4.5:1, respectively, predominantly attached to the partial ester at the site of a primary hydroxyl group. The chain length of the polyoxyalkylene group is essentially governed by amount of the alkylene oxide employed in relation to the partial ester. On this basis, a range of from 15 to 100 moles of the alkylene oxide per mole of the partial ester is broadly applicable.

The random nature of the polyoxyalkylene chain is an important factor in providing liquid products and such is realized primarily by the manner in which the ethylene oxide and propylene oxide are reacted with the partial ester. The preferred mode consists of simultaneously adding both alkylene oxides in the selected ratio to the partial ester upon effecting the adduction reaction. Alternatively, the alkylene oxides can be added as a preformed mixture thereof. The process conditions otherwise applicable conform to standard practices observed in carrying out this reaction. Such include use of a suitable catalyst; e.g., an alkali metal hydroxide, and an operating temperature preferably in the order of about 150° to 180° C. The reaction is ordinarily conducted in a closed system at a pressure of from 2 to 10 atmospheres.

The nonionic surfactant is combined with that amount of the anionic surfactant which provides an overall composition denoted as "minimally irritating" to the eye in accordance with the Draize test. Maximum mean eye irritation scores of from 1 to about 18 are classified as conforming to this category of irritation. The general method for evaluating and scoring in accordance with this test is outlined in the J. Pharmacol. and Exp. Ther. 82, page 377 (1944) as well as in Section 191.12 of Federal Hazardous Substance Act. The ratio of nonionic to the anionic for achieving the indicated level of irritation is at least about one part by weight of the nonionic surfactant to one part of the anionic surfactant. This minimum ratio is applicable only for those compositions devoid of a foam stabilizer in either the form of an amine oxide or an alkanolamide. The applicable maximum ratio of nonionic to anionic is an aspect turning mainly on detergency and/or viscosity considerations and in that light is about 4:1, respectively.

The inclusion of a foam stabilizer of the types applicable for this purpose, notably the superamide, has the effect of increasing the eye irritation characteristics of the system beyond the normally to be expected. However, this increase can be compensated for by moderately increasing the minimum ratio of nonionic to anionic surfactant. Generally, the amount of foam stabilizer is based upon the amount of the anionic surfactant component present in the system, such being from about 20 to 25% of the anionic surfactant component. Amounts of the foam stabilizer less than the specified lower limit results in less than optimum foam stabilization properties. On the other hand, amounts of the stabilizer in excess of the higher limit specified is normally to be avoided because of the rinsing problems arising through the presence of such excessive amounts of the stabilizer. Thus, within the indicated range of stabilizer content, a minimum ratio of two parts by weight of the nonionic to one part by weight of the anionic surfactant will provide an overall composition having a mean eye irritation score in the "minimally" category.

As mentioned above, an important feature of the present invention resides in the ability to regulate the viscosity of aqueous solutions of the contemplated detergent systems by appropriate selection of the nonionic surfactant component. This feature is illustrated in the accompanying drawing. In this graphical representation, viscosity is plotted against percent solids of a typical aqueous shampoo system. The active content of the system used for this illustration corresponds to formulation No. 2 of Example II and, as such, includes on a solid basis 39.6 wt. % SLES, 64.3% of the nonionic surfactant and 6.1% of a commercial superamide. Basically, two types of nonionic surfactants were used in obtaining the plot data for this drawing. The preparation of these surfactants is given in Example I.

As can be noted from the drawing, the viscosity of the aqueous system is primarily dependent upon the nature of the nonionic surfactant and the percent of total solids in the system. As shown, the greatest build-up of viscosity can be achieved by using a 82-mole polyoxyalkylene adduct of an equilibrated reaction mixture of mono- and digylcerides derived from tallow wherein the polyoxyalkylene chain is composed of randomly distributed oxyethylene and oxypropylene residues in the ratio of 3:1 respectively. On the other hand, substituting a similar 35-mole oxyalkylene adduct of a comparable partial ester mixture of coconut fatty acids therefore permits higher solids levels in obtaining the corresponding viscosity of the use of said tallowate adduct. Further, it can be seen that control of the viscosity characteristics can be realized within the normal range of solids concentration of a detergent system by judiciously blending these two representative partial glycerol ester adducts. It is important to note that the drawing is given for illustrative purposes only and not necessarily meant to limit the invention to the use of the two types of nonionic surfactants represented therein.

The following working examples support the foregoing in providing a description for the best mode contemplated for carrying out the present invention. While forming no part of this invention, Example I illustrates in detail the preferred manner in which representative nonionic surfactants useful in the practice of the invention can be prepared; namely, the types referred to in the drawings. Example II serves to illustrate the low degree of eye irritation properties associated with typical detergent shampoo systems embraced by the present invention. Consistent with the disclosure heretofore given, all parts and percentages specified in the working examples are by weight.

EXAMPLE I

35(3EO/PO) Glycerol Cocoate

Into a suitable reaction vessel were charged 2335 parts (3.57 moles) refined coconut oil, 345 parts (3.75 moles) glycerin, and 5.4 parts of 50% aqueous KOH. With stirring, the reaction mixture was heated to 110° C. and held for one hour under 20 mm vacuum. The reaction mixture was then heated to 165° C. with a nitrogen sparge and held for 3 hours.

To a pressure vessel was charged 140 parts (0.33 mole) of the above mono- and diglyceride mixture. The reactor was purged twice with nitrogen and heated to 150° C. A preformed mixture of alkylene oxides containing 385 parts (8.75 moles) of ethylene oxide and 169 parts (2.91 moles) of propylene oxide was added over an 8-hour period while maintaining the temperature at 150°–160° C. Upon cooling the reaction mixture to about 110° C., 25% aqueous sulfuric acid was added for neutralization (pH 8) and the reaction mixture then filtered.

82(3EO/PO) Glycerol Tallowate

In a manner described above one mole of tallow was reacted with 1.05 mole of glycerin in the presence of potassium hydroxide to provide a mixture of tallow mono- and diglycerides. Following stripping to remove moisture, a mole aliquot of the partial ester mixture was then reacted with a preformed mixture of 61.5 moles of ethylene oxide and 20.5 moles of propylene oxide as per the procedure outlined above whereupon the alkoxylated product was cooled, stripped and filtered.

EXAMPLE II

An 82(3EO/PO) glycerol cocoate (Nonionic A) and a 35(2EO/PO) glycerol tallowate (Nonionic B) were prepared following the general procedure outlined in Example I. Aqueous shampoo formulations were prepared using said adducts as the nonionic surfactant component thereof and tested for eye irritation properties in accordance with the Draize method. The indicated foam stabilizer in formulation No. 2 was a commercial coco superamide (VARAMIDE MA1—ASHLAND CHEMICAL CO.). Further details relative to the make-up of these systems and the test results obtained are set forth in the following Table I.

TABLE I

AQUEOUS SHAMPOO FORMULATIONS
WT. % OF ACTIVE COMPONENTS

| NO. | SLES | NONIONIC A | NONIONIC B | COCO SUPERAMIDE | MEAN IRR. SCORE |
| --- | --- | --- | --- | --- | --- |
| 1 | 9.1 | 18.2 | — | — | 5.3 |
| 2 | 8.3 | 18.0 | — | 1.7 | 4.7 |
| 3 | 9.1 | — | 18.2 | — | 4.7 |

What is claimed is:

1. A low eye and skin irritant detergent composition comprising:
    (a) an alkylene oxide adduct of a partial glycerol ester of a $C_{10}-C_{18}$ fatty acid having a monoglyceride content of from about 15 to 45 wt. % with diglycerides essentially constituting the balance, said adduct prepared by reacting one mole of the partial glycerol ester per 15 to 100 moles of ethylene oxide and propylene oxide in a molar ratio of 2:1 to 4.5:1, respectively; and
    (b) anionic surface-active agent selected from the group of salt of higher alkyl sulfate or salt of higher alkyl ether sulfate or salt of higher alkyl benzene sulfonate; and
wherein the weight ratio of (a) to (b) is between about 1:1 and 4:1, respectively.

2. A low eye and skin irritant detergent composition comprising:
    (a) an alkylene oxide adduct of a partial glycerol ester of a $C_{10}-C_{18}$ fatty acid having a monoglyceride content of from about 15 to 45 wt. % with diglycerides essentially constituting the balance, said adduct prepared by reacting one mole of the partial glycerol ester per 15 to 100 moles of ethylene oxide and propylene oxide in a molar ratio of 2:1 to 4.5:1, respectively;
    (b) anionic surface-active agent selected from the group of salt of higher alkyl sulfate or salt of higher alkyl ether surface or salt of higher alkyl benzene sulfonate; and
    (c) an alkanolamide foam stabilizing agent;
wherein the weight ratio of (b) to (c) is about 4:1 to 5:1, respectively, and wherein the weight ratio of (a) to (b) is about 2:1 to 5:1, respectively.

3. The detergent composition of claim 1 or 2 wherein said anionic surface-active agent is sodium lauryl sulfate, sodium lauryl ether sulfate, or sodium $C_{12}-C_{18}$ alkyl benzene sulfonate.

4. The composition of claim 1 or 2 wherein said partial glycerol ester has a monoglyceride content of about 25 to 35 wt. %.

5. The composition of claim 1 or 2 wherein said adduct is prepared by reacting about one mole of a partial glycerol ester of coconut oil per about 35 moles of ethylene oxide and propylene oxide in a molar ratio of about 3:1.

6. The composition of claim 1 or 2 wherein said adduct is prepared by reacting about one mole of a partial ester of tallow per about 82 moles of ethylene oxide and propylene oxide in a molar ratio of about 3:1.

7. The composition of claim 1 or 2 wherein the molar ratio of ethylene oxide to propylene oxide is about 3:1.

8. The composition of claim 1 or 2 being in the form of a dilute aqueous preparation.

* * * * *